United States Patent [19]

Franke et al.

[11] Patent Number: 4,678,811

[45] Date of Patent: Jul. 7, 1987

[54] SUBSTITUTED BENZYLETHERS, PESTICIDES CONTAINING THESE COMPOUNDS AND METHOD FOR THEIR PREPARATION

[75] Inventors: Helga Franke; Heinrich Franke; Hans-Rudolf Krüger; Hartmut Joppien, all of Berlin, Fed. Rep. of Germany

[73] Assignee: Schering Aktiengesellschaft, Berlin and Bergkamen, Fed. Rep. of Germany

[21] Appl. No.: 788,285

[22] Filed: Oct. 17, 1985

[30] Foreign Application Priority Data

Oct. 17, 1984 [DE] Fed. Rep. of Germany ....... 3438483

[51] Int. Cl.$^4$ .................... A01N 31/14; C07C 43/225; C07C 43/115

[52] U.S. Cl. .................... 514/721; 514/716; 514/919; 568/583; 568/586; 568/588; 568/645; 568/649; 568/654; 568/655; 568/656; 568/39; 568/45; 549/365; 549/471; 549/41; 548/346; 424/DIG. 10

[58] Field of Search ........... 568/645, 586, 39, 45, 568/583, 588, 649, 654, 655, 656; 514/721, 716

[56] References Cited

U.S. PATENT DOCUMENTS 3,966,824  6/1976  Metcalf et al. ............... 568/645
4,123,556  10/1978  Karrer ..................... 514/721 X
4,153,731  5/1979  Karrer .

FOREIGN PATENT DOCUMENTS 2085006  4/1982  United Kingdom ............... 514/721

*Primary Examiner*—Howard T. Mars
*Attorney, Agent, or Firm*—Millen & White

[57] ABSTRACT

New substituted benzyl-type ethers of formula I $$R_1 - \underset{\underset{R_2}{|}}{\overset{\overset{CHF_2}{|}}{C}} - CH_2 - X - \underset{}{\overset{\overset{R_3}{|}}{CH}} - R_4 \quad (I)$$

in which $R_1$ is aryl or aryl substituted by $C_{1-4}$-alkyl, halo-$C_{1-4}$-alkyl, phenyl-$C_{1-4}$-alkyl, $C_{2-4}$-alkenyl, halo-$C_{2-4}$-alkenyl, phenyl-$C_{2-4}$-alkenyl, $C_{2-4}$-alkynyl, halo-$C_{2-4}$-alkynyl, phenyl-$C_{2-4}$-alkynyl, $C_{1-4}$-alkoxy, halo-$C_{1-4}$-alkoxy, phenyl-$C_{1-4}$-alkoxy, $C_{2-4}$-alkenyloxy, halo-$C_{2-4}$-alkenyloxy, phenyl-$C_{2-4}$-alkenyloxy, $C_{2-4}$-alkynyloxy, halo-$C_{2-4}$-alkynyloxy, phenyl-$C_{2-4}$-alkynyloxy, alkylsulfonyloxy, haloalkylsulfonyloxy, arylsulfonyloxy, halo, cyano, nitro, aryloxy, haloaryloxy, $C_{1-4}$-alkyl-aryloxy, or nitroaryloxy, $R_2$ is hydrogen or $C_{1-4}$ alkyl, $R_3$ is hydrogen, cyano or ethynyl, $R_4$ is phenyl or pyridyl or one of these groups substituted by one or more of $C_{1-6}$-alkyl, halo-$C_{1-6}$-alkyl, phenyl-$C_{1-6}$-alkyl, $C_{1-6}$-alkyl interrupted by an O—, N— or S— atom, $C_{2-4}$-alkenyl, halo-$C_{2-4}$-alkenyl, phenyl-$C_{2-4}$-alkenyl, $C_{1-4}$-alkoxy, halo-$C_{1-4}$-alkoxy, phenyl-$C_{1-4}$-alkoxy, $C_{2-4}$-alkenyloxy, halo-$C_{2-4}$-alkenyloxy, phenyl-$C_{2-4}$-alkenyloxy, $C_{2-4}$-alkynyloxy, halo-$C_{2-4}$-alkynyloxy, phenyl-$C_{2-4}$-alkynyloxy, aryloxy, haloaryloxy, $C_{1-4}$-alkylaryloxy, arylamino, haloarylamino, $C_{1-4}$-alkylarylamino, aryl-N-$C_{1-4}$-alkylamino, aryl-N-$C_{1-4}$-acylamino, aroyl, haloaroyl, $C_{1-4}$-alkylaroyl, aryl, haloaryl, $C_{1-4}$-alkylaryl or halo and X is oxygen, sulfur, sulfinyl or sulfonyl, have valuable pesticidal properties.

46 Claims, No Drawings

SUBSTITUTED BENZYLETHERS, PESTICIDES CONTAINING THESE COMPOUNDS AND METHOD FOR THEIR PREPARATION

BACKGROUND OF THE INVENTION

This invention relates to new substituted benzyl ethers a process for their preparation and pesticidal compositions containing them.

Analogous compounds are already known (e.g., in DE-OS-31 17 510).

SUMMARY OF THE INVENTION

It is an object of the present invention to provide new active substances and pesticidal compositions containing them, especially insecticides, with improved properties.

Upon further study of the specification and appended claims, further objects and advantages of this invention will become apparent to those skilled in the art.

These objects have been achieved, according to the invention, by providing new substituted benzyl ethers and pesticidal compositions containing at least one such substituted benzyl ether.

These substituted benzyl-type ethers of this invention are of formula I

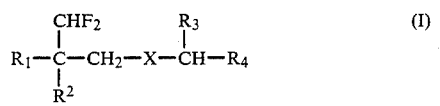

in which
- $R_1$ is aryl or aryl substituted by $C_{1-4}$-alkyl, halo-$C_{1-4}$-alkyl, phenyl-$C_{1-4}$-alkyl, $C_{2-4}$-alkenyl, halo-$C_{2-4}$-alkenyl, phenyl-$C_{2-4}$-alkenyl, $C_{2-4}$-alkynyl, halo-$C_{2-4}$-alkynyl, phenyl-$C_{2-4}$-alkynyl, $C_{1-4}$-alkoxy, halo-$C_{1-4}$-alkoxy, phenyl-$C_{1-4}$-alkoxy, $C_{2-4}$-alkenyloxy, halo-$C_{2-4}$-alkenyloxy, phenyl-$C_{2-4}$-alkenyloxy, $C_{2-4}$-alkynyloxy, halo-$C_{2-4}$-alkynyloxy, phenyl-$C_{2-4}$-alkynyloxy, alkylsulfonyloxy, haloalkylsulfonyloxy, arylsulfonyloxy, halo, cyano, nitro, aryloxy, haloaryloxy, $C_{1-4}$-alkyl-aryloxy, or nitroaryloxy,
- $R_2$ is hydrogen or $C_{1-4}$ alkyl,
- $R_3$ is hydrogen, cyano or ethynyl,
- $R_4$ is phenyl or pyridyl or one of these groups substituted by one or more of $C_{1-6}$-alkyl, halo-$C_{1-6}$-alkyl, phenyl-$C_{1-6}$-alkyl, $C_{1-6}$-alkyl interrupted by an O-, N- or S-atom, $C_{2-4}$-alkenyl, halo-$C_{2-4}$-alkenyl, phenyl-$C_{2-4}$-alkenyl, $C_{1-4}$-alkoxy, halo-$C_{1-4}$-alkoxy, phenyl-$C_{1-4}$-alkoxy, $C_{2-4}$-alkenyloxy, halo-$C_{2-4}$-alkenyloxy, phenyl-$C_{2-4}$-alkenyloxy, $C_{2-4}$-alkynyloxy, halo-$C_{2-4}$-alkynyloxy, phenyl-$C_{2-4}$-alkynyloxy, aryloxy, haloaryloxy, $C_{1-4}$-alkylaryloxy, arylamino, haloarylamino, $C_{1-4}$-alkylarylamino, aryl-N-$C_{1-4}$-alkylamino, aryl-N-$C_{1-4}$-acylamino, aroyl, haloaroyl, $C_{1-4}$-alkylaroyl, aryl, haloaryl, $C_{1-4}$-alkylaryl or halo and
- X is oxygen, sulfur, sulfinyl or sulfonyl.

DETAILED DISCUSSION

Suitable non-limiting aryl groups of $R_1$ include, in addition to phenyl, also 1-naphthyl, 2-naphthyl, benzofuran-5-yl, benzothiophen-5-yl, benzofuran-6-yl, benzothiophen-6-yl, benzoxazol-5-yl, benzoxazol-6-yl, indan-5-yl, indan-6-yl, 1,4-benzodioxan-6-yl, 1,3-benzodioxan-6-yl, 1,3-benzodioxan-7-yl, or 1,3-benzodioxol-5-yl and equivalents thereof. The preferred suitable aryl group in $R_4$ is phenyl.

In Formula I, halo includes F, Cl, Br and I. Generally there are 1–5 halo, phenyl, aryl or nitro groups where the presence of halo, phenyl or nitro is recited. Generally there are 1–5 substituents on the $R_4$ phenyl or pyridyl ring. Typically there is only one substituent per C- or hetero-atom. In all substituted groups, however, geminal substitution is also possible as are groups such as trichloromethyl, etc. Pyridyl as $R_4$ is generally attached to the rest of the molecule by one of its C-atoms.

All alkyl portions of the various groups in Formula I (e.g., alkyl, alkoxy, alkenyl, alkynyl, etc.), as appropriate, include methyl, ethyl, n- or i-propyl, n-, i-, sec- or t-butyl, a pentyl or a hexyl group. Suitable acyl groups preferably include alkanoyl groups.

The compounds of this invention have pesticidal, e.g., insecticidal and acaricidal activity, and are particularly useful in combating a variety of economically important insects, and acarids including animal ectoparasites. Non-limiting examples include Lepidoptera, e.g., *Spodoptera littoralis, Heliothis armigera*, and *Pieris brassicae;* Diptera, e.g., *Musca domestica, Ceratitis capitata, Erioischia brassicae, Lucilia sericata* and *Aedes aegypti;* Homoptera, including aphids, e.g., *Megoura viciae* and *Nilaparvata lugens;* Coleoptera, e.g., *Phaedon cochleariae, Anthonomus grandis* and corn rootworms (*Diabrotica* spp. e.g., *Diabrotica undecimpunctata*); Orthoptera, e.g., *Blattella germanica;* ticks, e.g., *Boophilus microplus,* and lice, e.g., *Damalinia bovis* and *Linognathus vituli;* as well as spider mites, e.g., *Tetranychus urticae* and *Panonychus ulmi*.

The compounds are distinguished by a surprisingly high level of activity against important pest species, which is greater than that of known pesticidal compositions having a similar mode of action.

The compounds according to the invention can be used at a concentration of 0.0005 to 5%, preferably from 0.001 to 0.1%, calculated as grams of active material per 100 ml of the composition.

The compounds of the invention can be used either alone or in admixture with each other or another insecticide. Optionally, other plant protection or pesticidal compositions, for example, insecticides, acaricides or fungicides can be added depending on the desired result.

An improvement in the intensity and speed of action can be obtained, for example, by addition of suitable adjuvants, such as organic solvents, wetting agents and oils. Such additives may allow a decrease in the dose stated above.

Suitable mixture adjustments include phospholipids, e.g., phosphatidylcholine, hydrated phosphatidycholines, phosphatidylethanolamine, N-acyl-phosphatidylethanolamines, phosphatidylinositol, phosphatidylserine, lysolecithin or phosphatidylglycerol.

The active ingredients and their mixtures can suitably be used, for example, as powders, dusts, granules, solutions, emulsions or suspensions, with the addition of liquid and/or solid carriers and/or diluents and, optionally, binding, wetting, emulsifying and/or dispersing adjuvants.

Suitable non-lmiting carriers include, for example, water, aliphatic and aromatic hydrocarbons, e.g., benzene, toluene, xylene, cyclohexanone, isophorone, dimethylsulfoxide, dimethylformamide, other mineral-oil fractions and plant oils.

Suitable solid carriers include mineral earths, e.g., tonsil, silica gel, talcum, kaolin, attapulgite, limestone, silicic acid and plant products, e.g., flours.

As surface-active agents there can be used for example calcium lignosulphonate, polyoxyethylenealkylphenyl ether, naphthalenesulphonic acids and their salts, phenolsulphonic acids and their salts, formaldehyde condensates, fatty alcohol sulphates, as well as substituted benzenesulphonic acids and their salts.

The percentage of the active ingredient(s) in the various preparations can vary within wide limits. For example, compositions can contain the percentages given above or even about 10 to 90 percent by weight active ingredients, and about 90 to 10 percent by weight liquid or solid carriers, as well as, optionally up to 20 percent by weight or surfactant.

The agents can be applied in customary fashion, for example with water as the carrier in spray mixture volumes of approximately 100 to 3,000 l/ha where application to fields is involved. The agents can be applied using low-volume or ultra-low-volume techniques or in the conventional form of so-called microgranules. In general, they are applied analogously to the known agent ethoproxyfen.

The preparation of these formulations can be carried out in a known manner, for example by milling or mixing processes. Optionally, individual components can be mixed just before use for example by the so-called commonly used tank-mixing method.

Formulations can be prepared, for example, from the following ingredients.

| | | |
|---|---|---|
| A. | 20 | percent by weight active ingredient |
| | 35 | percent by weight bentonite |
| | 8 | percent by weight calcium lignosulphonate |
| | 2 | percent by weight of the sodium salt of N—methyl-N—oleyltaurine |
| | 35 | percent by weight silicic acid |
| B. | 20 | percent by weight active ingredient |
| | 75 | percent by weight isophorone |
| | 5 | percent by weight of an emulsifier mixture of calcium phenylsulphonate and fatty alcohol polygylcol ether |
| C. | 80 | percent by weight active ingredient |
| | 15 | percent weight kaolin |
| | 5 | percent by weight surface-active agent based on the sodium salt of N—methyl-N—oleyltaurine and the calcium lignosulphonate |
| D. | 45 | percent by weight active ingredient |
| | 5 | percent by weight sodium aluminum silicate |
| | 15 | percent by weight cetylpolyglycol ether with 8 moles ethylene oxide |
| | 2 | percent by weight spindle oil |
| | 10 | percent by weight polyethylene glycol |
| | 23 | parts water |

The compounds of the invention can be prepared for example by
(a) reacting a compound of the formula II

with a compound of formula III

(b) reacting a compound of formula IV

with a compund of formula (V)

in the presence of a base and in the presence of a solvent wherein $R_1$, $R_2$, $R_3$, $R_4$, and X have the meanings given above, Z is a leaving group, such as for example, halogen, methanesulphonate or toluenesulphonate and M is hydrogen or a monovalent metal equivalent.

The etherification is generally carried out in solution. Bases that are suitable include metal alcoholates such as for example potassium tert-butylate, metall hydrides, such as for example sodium hydride, metal amides, such as for example lithium diisopropylamide and metal alkyl compounds, such as for example ethyl magnesium bromide or butyl lithium.

Suitable solvents, as opposed to the reactants, especially the bases, include inert substances such as aliphatic and aromatic hydrocarbons such as for example hexane, benzene, or toluene and ethers such as for example diethyl ether, tetrahydrofuran or dimethoxyethane. Suitable further amides include dimethylformamide, N-methylpyrrolidone or hexamethylphosphoric acid triamide.

The etherification can futhermore be carried out in a two-phase system using a catalyst and preferably a solvent. Alkali metal hydroxides or carbonates can be used as bases alone or in aqueous solution. The reactants themselves may be suitable as solvents as long as they are liquid; otherwise inert substances can be used, which are immiscible with water and inert to bases e.g., aliphatic and aromatic hydrocarbons, such as for example hexane, benzene or toluene. Preferred catalysts are crown ethers and quaternary ammonium salts.

The reaction is carried out at a temperature of $-78°$ to $140°$ C., preferably at $20°-80°$ C. and usually at atmospheric pressure.

Compounds where $R_3$ is cyano, can be prepared from the corresponding compounds where $R_3$ is hydrogen, which are brominated with N-bromosuccinimide and the attached bromine is exchanged for cyano.

The alcohols used as starting materials can be prepared by reduction of the corresponding nitrile, aldehyde, carboxylic acid or carboxylic acid ester. The reduction can be carried out by known methods using metal hydrides, e.g., lithium aluminum hydride or an alkyl aluminum hydride, e.g., diisobutyl aluminum hydride. The requisite nitriles can be prepared by alkylation of the corresponding arylacetonitrile with $CHClF_2$.

The thioalcohols, halides, tosylates and mesylates which are used and all starting materials used in the reactions of this invention are known or can be prepared by known methods (e.g., in DE-OS 3,117,510 and Tetrahedron Letters 52 (1978)5225).

The compounds of the invention can exist in various isomeric forms. The invention includes all individual isomers as well as mixtures of them.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius; and all parts and percentages are by weight, unless otherwise indicated.

EXAMPLE 1

2-(4-Chlorophenyl)-2-difluoromethyl-1-(4-fluoro-3-phenoxybenzyloxy)propane 0.44 g (10 mmol) Sodium hydride dispersion (55%) was freed from oil by washing three times with dry toluene. It was suspended in 10 ml dry dimethoxyethane and then, with stirring, 1.77 g (8.0 mmol) 2-(4-chlorophenyl)-2-difluoromethylpropanol and 2.24 g (8.0 mmol) 4-fluoro-3-phenoxybenzyl bromide added. After stirring for five hours at room temperature a thin layer chromatogram (Merck DC silica gel 60F$_{254}$ plate, using hexane/ethyl acetate 1:1 as eluant, R$_f$ 0.57) showed that no starting material was present.

The mixture was poured into ice-water, extracted twice with ether, the extract dried with magnesium sulphate and evaporated. After silica-gel chromatography using hexane/ethyl acetate, 2.96 g of a colorless oil remained i.e. 88% of theory.

Refractive index n$_D^{20}$: 1.5570

| Analysis | C | H | Cl | F |
|---|---|---|---|---|
| Calculated | 65.64% | 4.80% | 8.42% | 13.54% |
| Found | 65.67% | 4.84% | 8.66% | 13.54% |

In a similar manner the following compounds according to the invention were prepared.

| Example No. | Compound | Physical constant n$_D^{20}$ or Mp. |
|---|---|---|
| 2 | 2-(4-Chlorophenyl)-2-difluoromethyl-1-(3-phenoxybenzyloxy)propane | 1.5659 |
| 3 | 2-Difluoromethyl-2-(4-methylphenyl)-1-(3-phenoxybenzyloxy)propane | 1.5596 |
| 4 | 2-Difluoromethyl-1-(4-fluoro-3-phenoxybenzyloxy)-2-(4-methoxyphenyl)propane | 1.5581 |
| 5 | 2-Difluoromethyl-2-(4-methoxyphenyl)-1-(3-phenoxybenzyloxy)propane | 1.5615 |
| 6 | 2-Difluoromethyl-2-(4-fluorophenyl)-1-(4-fluoro-3-phenoxybenzyloxy)propane | 1.5427 |
| 7 | 2-Difluoromethyl-2-(4-fluorophenyl)-1-(3-phenoxybenzyloxy)propane | 1.5520 |
| 8 | 2-Difluoromethyl-2-(4-ethoxyphenyl)-1-(3-phenoxybenzyloxy)propane | 1.5575 |
| 9 | 2-Difluoromethyl-2-(4-ethoxyphenyl)-1-(4-fluoro-3-phenoxybenzyloxy)propane | 1.5486 |
| 10 | 2-Difluoromethyl-2-(4-ethoxyphenyl)-1-(6-phenoxypyridin-2-ylmethoxy)propane | 1.5557 |
| 11 | 2-Difluoromethyl-2-(4-fluorophenyl)-1-(6-phenoxypyridin-2-ylmethoxy)propane | 1.5502 |
| 12 | 2-Difluoromethyl-1-(3-phenoxybenzyloxy)-2-(4-n-propoxyphenyl)propane | 1.5532 |
| 13 | 2-Difluoromethyl-1-(4-fluoro-3-phenoxybenzyloxy)-2-(4-n-propoxyphenyl)propane | 1.5439 |
| 14 | 2-Difluoromethyl-2-(4-isopropoxyphenyl)-1-(3-phenoxybenzyloxy)propane | 1.5528 |
| 15 | 2-Difluoromethyl-1-(4-fluoro-3-phenoxybenzyloxy)-2-(4-isopropoxyphenyl)propane | 1.5440 |
| 16 | 2-(4-n-Butoxyphenyl)-2-difluoromethyl-1-(3-phenoxybenzyloxy)propane | 1.5492 |
| 17 | 2-(4-n-Butoxyphenyl)-2-difluoromethyl-1-(4-fluoro-3-phenoxybenzyloxy)propane | 1.5410 |
| 18 | 2-(4-Allyloxyphenyl)-2-difluoromethyl-1-(3-phenoxybenzyloxy)propane | 1.5615 |
| 19 | 2-(4-Allyloxyphenyl)-2-difluoromethyl-1-(4-fluoro-3-phenoxybenzyloxy)propane | 1.5530 |
| 20 | 2-Difluoromethyl-2-[4-(2-fluoroethoxy)-phenyl]-1-(3-phenoxybenzyloxy)propane | 1.5550 |
| 21 | 2-Difluoromethyl-1-(4-fluoro-3-phenoxybenzyloxy)-2-(4-propargyloxyphenyl)propane | 1.5547 |
| 22 | 2-(4-Difluoromethoxyphenyl)-2-difluoromethyl-1-(3-phenoxybenzyloxy)propane | 1.5382 |
| 23 | 2-(4-Difluoromethoxyphenyl)-2-difluoromethyl-1-(4-fluoro-3-phenoxybenzyloxy)propane | 1.5287 |
| 24 | 2-(4-Bromophenyl)-2-difluoromethyl-1-(3-phenoxybenzyloxy)propane | 1.5767 |
| 25 | 2-(4-Bromophenyl-2-difluoromethyl-1-(4-fluro-3-phenoxybenzyloxy)propane | 1.5681 |
| 26 | 2-(4-tert.-Butylphenyl)-2-difluoromethyl-1-(3-phenoxybenzyloxy)propane | 1.5484 |
| 27 | 2-(4-tert.-Butylphenyl)-2-difluoromethyl-1-(4-fluoro-3-phenoxybenzyloxy)propane | 1.5404 |
| 28 | 2-Difluoromethyl-2-(2-naphthyl)-1-(3-phenoxybenzyloxy)propane | 1.5969 |
| 29 | 2-Difluoromethyl-2-(2-naphthyl)-1-(4-fluoro-3-phenoxybenzyloxy)propane | 1.5847 |
| 30 | 2-Difluoromethyl-2-(3,4-dimethoxyphenyl)-1-(3-phenoxybenzyloxy)propane | 1.5602 |
| 31 | 2-Difluoromethyl-2-(3,4-dimethoxyphenyl)-1-(4-fluoro-3-phenoxybenzyloxy)propane | 1.5555 |
| 32 | 2-(1,3-Benzodioxol-5-yl)-2-difluoromethyl-1-(3-phenoxybenzyloxy)propane | 1.5692 |
| 33 | 2-(1,3-Benzodioxol-5-yl)-2-difluoromethyl-1-(4-fluoro-3-phenoxybenzyloxy)propane | 1.5602 |
| 34 | 2-Difluoromethyl-1-(4-fluoro-3-phenoxybenzyloxy)-2-[4-(2-fluoroethoxy)phenyl]propane | 1.5460 |
| 35 | 2-Difluoromethyl-1-[3-(2-fluoroethoxy)-benzyloxy]-2-(4-ethoxyphenyl)propane | 1.5240 |
| 36 | 2-Difluoromethyl-1-[4-(2-fluoroethoxy)-benzyloxy]-2-(4-ethoxyphenyl)propane | 71–72° C. |
| 37 | 2-Difluoromethyl-2-(4-ethoxyphenyl)-1-[3-(N—methylanilino)benzyloxy]-propane | 1.5771 |
| 38 | 2-Difluoromethyl-1-(3-phenoxybenzyloxy)-2-[4-(2,2,2-trifluoroethoxy)phenyl]-propane | 1.5283 |
| 39 | 2-Difluoromethyl-1-(4-fluoro-3-phenoxybenzyloxy)-2-[4-(2,2,2-trifluoroethoxy)-phenyl]propane | 1.5209 |
| 40 | 2-Difluoromethyl-2-(4-ethoxyphenyl)-1-(3-phenoxybenzylthio)propane | 1.5783 |
| 41 | 2-Difluoromethyl-2-(3,4-dimethoxyphenyl)-1-(6-phenoxypyridin-2-ylmethoxy)propane | 81.5–83.5° C. |
| 42 | 2-(4-Bromophenyl)-2-difluoromethyl-1-(6-phenoxypyridin-2-yl-methoxy)propane | 1.5750 |
| 43 | 2-Difluoromethyl-2-(2-naphthyl)-1-(6-phenoxypyridin-2-ylmethoxy)propane | 1.5951 |
| 44 | 2-(4-Allyloxyphenyl)-2-difluoromethyl-1-(6-phenoxypyridin-2-ylmethoxy)propane | 1.5600 |
| 45 | 2-Difluoromethyl-1-(6-phenoxypyridin-2-ylmethoxy)-2-(4-n-propoxyphenyl)propane | 1.5509 |

| Example No. | Compound | Physical constant $n_D^{20}$ or Mp. |
|---|---|---|
| 46 | 2-Difluoromethyl-2-(4-ethoxyphenyl)-1-(2-methyl-3-phenylbenzyloxy)propane | 1.5621 |

The compounds of the invention are colorless oils, with the exception of a few compounds which are solids, that are highly soluble in most organic solvents but practically insoluble in water.

The following Examples illustrate the possible uses of the compounds of the invention, as mentioned above.

EXAMPLE 47

Activity against larvae of diamond-backed moth (*Plutella xylostella*)

The compounds of the invention were made up as aqueous emulsions at a concentration of 0.1%. Cabbage leaves, placed in polystyrene petri dishes, were sprayed with these preparations (4 mg spray/cm²). After the sprayed surface had dried, 10 young larvae of the diamond-backed moth (*Plutella xylostella*) were placed in each petri dish and thereby exposed to the treated food in the closed dishes for two days. The % mortality of the larvae after two days indicated the level of activity. The results are summarized in the following table.

| Compounds of the invention | Concentration (%) | Activity (%) |
|---|---|---|
| 2-(4-Chlorophenyl)-2-difluoromethyl-1-(4-fluoro-3-phenoxybenzyloxy)propane | 0.1 | 100 |
| 2-(4-Chlorophenyl)-2-difluoromethyl-1-(3-phenoxybenzyloxy)propane | 0.1 | 100 |
| 2-Difluoromethyl-2-(4-methylphenyl)-1-(3-phenoxybenzyloxy)propane | 0.1 | 100 |
| 2-Difluoromethyl-1-(4-fluoro-3-phenoxybenzyloxy)-2-(4-methoxyphenyl)propane | 0.1 | 100 |
| 2-Difluoromethyl-2-(4-methoxyphenyl)-1-(3-phenoxybenzyloxy)propane | 0.1 | 100 |
| 2-Difluoromethyl-2-(4-fluorophenyl)-1-(4-fluoro-3-phenoxybenzyloxy)propane | 0.1 | 100 |
| 2-Difluoromethyl-2-(4-fluorophenyl)-1-(3-phenoxybenzyloxy)propane | 0.1 | 100 |
| 2-Difluoromethyl-2-(4-ethoxyphenyl)-1-(3-phenoxybenzyloxy)propane | 0.1 | 100 |
| 2-Difluoromethyl-2-(4-ethoxyphenyl)-1-(4-fluoro-3-phenoxybenzyloxy)propane | 0.1 | 100 |
| 2-Difluoromethyl-2-(4-ethoxyphenyl)-1-(6-phenoxypyridin-2-ylmethoxy)propane | 0.1 | 100 |
| 2-Difluoromethyl-2-(4-fluorophenyl)-1-(6-phenoxypyridin-2-ylmethoxy)propane | 0.1 | 100 |
| 2-Difluoromethyl-2-(3,4-dimethoxyphenyl)-1-(3-phenoxybenzyloxy)propane | 0.1 | 65 |
| 2-Difluoromethyl-2-(3,4-dimethoxyphenyl)-1-(4-fluoro-3-phenoxybenzyloxy)propane | 0.1 | 94 |
| 2-(1,3-Benzodioxol-5-yl)-2-difluoromethyl-1-(3-phenoxybenzyloxy)propane | 0.1 | 100 |
| 2-(1,3-Benzodioxol-5-yl)-2-difluoromethyl-1-(4-fluoro-3-phenoxybenzyloxy)propane | 0.1 | 65 |
| 2-Difluoromethyl-2-(4-ethoxyphenyl)-1-[3-(N—methylanilino)benzyloxy]propane | 0.1 | 88 |
| 2-Difluoromethyl-2-(2-naphthyl)-1-(3-phenoxybenzyloxy)propane | 0.1 | 100 |
| 2-Difluoromethyl-2-(2-naphthyl)-1-(4-fluoro-3-phenoxybenzyloxy)propane | 0.1 | 100 |
| 2-Difluoromethyl-2-(2-naphthyl)-1-(6-phenoxypyridin-2-ylmethoxy)propane | 0.1 | 90 |
| 2-(4-Difluoromethyoxyphenyl)-2-difluoromethyl-1-(3-phenoxybenzyloxy)propane | 0.1 | 100 |
| 2-(4-Difluoromethoxyphenyl)-2-difluoromethyl-1-(4-fluoro-3-phenoxybenzyloxy)propane | 0.1 | 100 |
| 2-(4-tert.-Butylphenyl)-2-difluoromethyl-1-(3-phenoxybenzyloxy)propane | 0.1 | 60 |
| 2-(4-tert.-Butylphenyl)-2-difluoromethyl-1-(4-fluoro-3-phenoxybenzyloxy)propane | 0.1 | 70 |
| 2-Difluoromethyl-2-(4-ethoxyphenyl)-1-(2-methyl-3-phenylbenzyloxy)propane | 0.1 | 85 |
| 2-Difluoromethyl-1-(4-fluoro-3-phenoxybenzyloxy)-2-(4-propargyloxyphenyl)propane | 0.1 | 100 |
| 2-Difluoromethyl-1-(3-phenoxybenzyloxy)-2-[4-(2,2,2-trifluoroethoxy)phenyl]propane | 0.1 | 100 |
| 2-Difluoromethyl-1-(4-fluoro-3-phenoxybenzyloxy)-2-[4-(2,2,2-trifluoroethoxy)phenyl]propane | 0.1 | 100 |
| 2-Difluoromethyl-2-[4-(2-fluoroethoxy)phenyl]-1-(3-phenoxybenzyloxy)propane | 0.1 | 100 |
| 2-Difluoromethyl-1-(4-fluoro-3-phenoxybenzyloxy)-2-[4-(2-fluoroethoxy)phenyl]propane | 0.1 | 100 |
| 2-Difluoromethyl-1-[3-(2-fluoroethoxy)benzyloxy]-2-(4-ethoxyphenyl)propane | 0.1 | 100 |
| 2-Difluoromethyl-2-(4-ethoxyphenyl)-1-3-phenoxybenzylthio)propane | 0.1 | 100 |
| 2-Difluoromethyl-1-[4-(2-fluoroethoxy)benzyloxy]-2-(4-ethoxyphenyl)propane | 0.1 | 100 |
| 2-Difluoromethyl-1-(3-phenoxy-benzyloxy)-2-(4-n-propoxyphenyl)propane | 0,1 | 100 |
| 2-Difluoromethyl-1-(4-fluoro-3-phenoxybenzyloxy)-2-(4-n-propoxyphenyl)propane | 0,1 | 100 |
| 2-Difluoromethyl-2-(4-isopropoxyphenyl)-1-(3-phenoxy-benzyloxy)propane | 0,1 | 100 |
| 2-Difluoromethyl-1-(4-fluoro-3-phenoxybenzyloxy)-2-(4-isopropoxyphenyl)propane | 0,1 | 100 |
| 2-(4-n-Butoxyphenyl)-2-difluoromethyl-1-(3-phenoxybenzyloxy)propane | 0,1 | 100 |
| 2-(4-n-Butoxyphenyl)-2-difluoromethyl-1-(4-fluoro-3-phenoxybenzyloxy)propane | 0,1 | 100 |
| 2-(4-Allyloxyphenyl)-2-difluoromethyl-1-(3-phenoxybenzyloxy)propane | 0,1 | 100 |
| 2-(4-Allyloxyphenyl)-2-difluoromethyl-1-(4-fluoro-3-phenoxybenzyloxy)propane | 0,1 | 100 |
| 2-Difluoromethyl-2-(3,4-dimethoxyphenyl)-1-(6-phenoxypyridin-2-ylmethoxy)propane | 0,1 | 65 |
| 2-(4-Bromophenyl)-2-difluoromethyl-1-(6-phenoxy-pyridin-2-ylmethoxy)propane | 0,1 | 100 |
| 2-(4-Bromophenyl)-2-difluoromethyl-1-(3-phenoxybenzyloxy)propane | 0,1 | 100 |
| 2-(4-Bromophenyl)-2-difluoromethyl-1-(4-fluoro-3-phenoxybenzyloxy)propane | 0,1 | 100 |
| 2-(4-Allyloxyphenyl)-2-difluoromethyl-1-(6-phenoxypyridin-2-ylmethoxy)propane | 0,1 | 100 |
| 2-Difluoromethyl-2-(4-ethoxyphenyl)-1-(2-methyl-3-phenylbenzyloxy)propane | 0,1 | 85 |

EXAMPLE 48

Activity against larvae (L2) of the cotton army worm (*Spodoptera littoralis*)

Compounds of the invention as well as a comparative compound were made up as aqueous emulsions at a concentration of 0.001%. Leaflet pairs of beans (*Vicia fabae*) as well as 10 larvae (L2) of the cotton army worm (*Spodoptera littoralis*) per experiment were sprayed with 4 mg spray/cm² of these preparations in polystyrene petri dishes. The closed petri dishes were left in the laboratory under extended daylight conditions for two days. The % mortality of the larvae after two days indicated the level of activity. Results are summarized in the following table.

| Compounds of the invention | Concentration (%) | Activity (%) |
|---|---|---|
| 2-Difluoromethyl-2-(4-ethoxyphenyl)-1-(3-phenoxybenzyloxy)propane | 0.001 | 80 |
| 2-Difluoromethyl-2-(4-ethoxyphenyl)-1-(4-fluoro-3-phenoxybenzyloxy)propane | 0.001 | 100 |
| 2-(4-Difluoromethoxyphenyl)-2-difluoromethyl-1-(4-fluoro-3-phenoxybenzyloxy)propane | 0.001 | 100 |
| Comparative product from DE-OS 31 17 510 | | |
| 2-(4-Ethoxyphenyl)-2-methyl-1-(3-phenoxybenzyloxy)propane | 0.001 | 55 |

EXAMPLE 49

Ovicidal activity against eggs of the cotton army worm (*Spodoptera littoralis*)

The compounds of the invention to be applied as well as a comparative material were made up into aqueous emulsions of desired concentration. One day old eggs that had been laid on filter paper by fertilized female moths were dipped in the preparations until they were completely wet and then placed in closed petri dishes for four days. The % inhibition of hatching of the eggs in comparison with untreated eggs indicates the level of activity.

Results are summarized in the following table.

| Compounds of the invention | Concentration (%) | Activity (%) |
|---|---|---|
| 2-Difluoromethyl-2-(4-ethoxyphenyl)-1-(4-fluoro-3-phenoxybenzyloxy)propane | 0.0025 | 90 |
| | 0.0010 | 50 |
| Comparative product from DE-OS 31 17 510 | | |
| 2-(4-Ethoxyphenyl)-2-methyl-1-(3-phenoxybenzyloxy)propane | 0.0025 | 10 |
| | 0.0010 | 0 |

EXAMPLE 50

Activity against larvae of the diamond-backed moth (*Plutella xylostella*)

Compounds of the invention as well as a comparative substance were made up into aqueous emulsions at concentrations of 0.0064, 0.0025 and 0.001%. Cabbage leaves in polystyrene petri dishes were sprayed with these preparations (4 mg spray/cm²). After the sprayed surface had dried, 10 young larvae of the diamond-backed moth (*Plutella xylostella*) were placed in each petri dish and thereby exposed to the treated food in the closed petri dishes for two days.

The % mortality of the larvae after two days indicated the level of activity. The results are summarized in the following table.

| Compounds of the invention | Concentration (%) | Activity (%) |
|---|---|---|
| 2-Difluoromethyl-2-(4-ethoxyphenyl)-1-(4-fluoro-3-phenoxybenzyloxy)propane | 0.0064 | 100 |
| | 0.0025 | 100 |
| | 0.001 | 80 |
| 2-(4-Difluoromethoxyphenyl)-2-difluoromethyl-1-(4-fluoro-3-phenoxybenzyloxy)propane | 0.0064 | 100 |
| | 0.0025 | 100 |
| | 0.001 | 80 |
| Comparative material of DE-OS 31 17 510 | | |
| 2-(4-Ethoxyphenyl)-2-methyl-1-(3-phenoxybenzyloxy)propane | 0.0064 | 90 |
| | 0.0025 | 70 |

EXAMPLE 51

Activity against motile stages and eggs of the two spotted spider mite (*Tetranychus urticae*)

Compounds of the invention as well as a comparative substance were made up to an aqueous emulsion at a concentration of 0.1%. Dwarf bean plants (*Phaseolus vulgaris*) in the primary leaf stage, which had been infested with spider mites (*Tetranychus urticae*), were sprayed with these preparations until they were dripping wet and left in a laboratory for seven days. After this the % mortality of the motile stages on the one hand and the eggs on the other hand were estimated using a magnifying glass.

The results are summarized in the following table.

| Compounds of the invention | Concentration (%) | Activity % against motile stages/eggs of *Tetranychus urticae* |
|---|---|---|
| 2-(4-Chlorophenyl)-2-difluoromethyl-1-(4-fluoro-3-phenoxybenzyloxy)propane | 0.1 | 95/40 |
| 2-Difluoromethyl-2-(4-fluorophenyl)-1-(4-fluoro-3-phenoxybenzyloxy)propane | 0.1 | 100/0 |
| 2-Difluoromethyl-2-(4-ethoxyphenyl)-1-(4-fluoro-3-phenoxybenzyloxy)propane | 0.1 | 75/25 |
| 2-Difluoromethyl-2-(4-fluorophenyl)-1-(6-phenoxypyridin-2-ylmethoxy)propane | 0.1 | 93/94 |
| 2-(4-Difluoromethoxyphenyl)-2-difluoro-methyl-1-(4-fluoro-3-phenoxybenzyloxy)propane | 0.1 | 100/0 |
| Comparative substance of DE-OS 31 17 510 | | |
| 2-(4-Ethoxyphenyl)-2-methyl-1-(3-phenoxybenzyloxy)propane | 0.1 | 38/4 |

EXAMPLE 52

Insecticidal and acaricidal activity against *Boophilus microplus* (1), *Lucilia sericata* (2) *Musca domestica* (3) and *Blattella germanica* (4)

1. 9 cm diameter filter papers were impregnated with 1 ml aliquots of acetone solutions of test compound at various concentrations. The papers were allowed to dry and then folded into envelopes in which cattle tick larvae, (*Boophilus microplus*) were enclosed and held at 25° C. and 80% R.H. for 48 hours. The percentage mortality of tick larvae was then recorded and compared with controls.

The controls gave less than 5% mortality whereas compounds of Examples 4, 5, 8, 10, 11, 17, 24, 25, 27, 32, 33, 42 and 45 had an $LD_{50}$ of less than 100 ppm.

2. 1 ml aliquots of an acetone solution containing test compound at various concentrations were applied to cotton wool dental rolls 1 cm×2 cm, contained in glass vials 2 cm diameter×5 cm long. After drying, the treated materials were then impregnated with 1 ml of nutrient solution, infested with first instar larvae of sheep blow fly (*Lucilia sericata*), closed by a cotton wool plug and held at 25° C. for 24 hours. For the controls the mortality was <5% whereas the compounds of Examples 4, 5, 8, 9, 10, 32 and 33 had an $LC_{50}$ of less than 100 ppm.

3. Aliquots of acetone solutions of test compounds at various concentrations were applied to 9 cm diameter filter papers placed in the bottom of 9 cm diameter petri dishes closed by glass lids. After evaporation of solvent, the treated surfaces, together with control treated with acetone alone, were then infested with adult houseflies, (*Musca domestica*) and held at 22° C. for 24 hours.

The percentage mortality of the insects was then recorded. Less than 5% mortality resulted in the control treatments whereas the $LD_{50}$ of compounds of Examples 4, 9, 15, 25, 38 and 39 was less than 100 mg/m².

4. Aliquots of acetone solutions of test compounds at various concentrations were applied to glass plates (10 cm × 10 cm). After evaporation of solvent, the treated surfaces, together with controls treated with acetone alone, were then infested with second instar nymphs of the German cockroach, (*Bllattella germanica*), retained on the treated surface within PTFE-coated glass rings 6 cm in diameter and held for 24 hours at 22° C. The percentage mortality of the insects was then recorded.

Less than 5% mortality resulted in the control treatments whereas the $LD_{50}$ of compounds of Examples 4, 5, 8, 9, 10, 11, 17, 18, 19, 22, 23, 24, 32, 33, 38 and 39 was less than 100 mg/m².

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

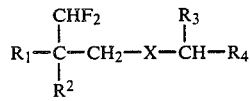

wherein
$R_1$ is aryl or aryl substituted by $C_{1-4}$-alkyl, halo-$C_{1-4}$-alkyl, phenyl-$C_{1-4}$-alkyl, $C_{2-4}$-alkenyl, halo-$C_{2-4}$-alkenyl, phenyl-$C_{2-4}$-alkenyl, $C_{2-4}$-alkynyl, halo-$C_{2-4}$-alkynyl, phenyl-$C_{2-4}$-alkynyl, $C_{1-4}$-alkoxy, halo-$C_{1-4}$-alkoxy, phenyl-$C_{1-4}$-alkoxy, $C_{2-4}$-alkenyloxy, halo-$C_{2-4}$-alkenyloxy, phenyl-$C_{2-4}$-alkenyloxy, $C_{2-4}$-alkynyloxy, halo-$C_{2-4}$-alkynyloxy, phenyl-$C_{2-4}$-alkynyloxy, halo, nitro, aryloxy, haloaryloxy, $C_{1-4}$-alkyl-aryloxy, or nitroaryloxy,
$R_2$ is hydrogen or $C_{1-4}$ alkyl,
$R_3$ is hydrogen, or ethynyl,
$R_4$ is phenyl or or phenyl substituted by one or more of $C_{1-6}$-alkyl, halo-$C_{1-6}$-alkyl, phenyl-$C_{1-6}$-alkyl, $C_{1-6}$-alkyl interrupted by an O-, atom, $C_{2-4}$-alkenyl, halo-$C_{2-4}$-alkenyl, phenyl-$C_{2-4}$-alkenyl, $C_{1-4}$-alkoxy, halo-$C_{1-4}$-alkoxy, phenyl-$C_{1-4}$-alkoxy, $C_{2-4}$-alkenyloxy, halo-$C_{2-4}$-alkenyloxy, phenyl-$C_{2-4}$-alkenyloxy, $C_{2-4}$-alkynyloxy, halo-$C_{2-4}$-alkynyloxy, phenyl-$C_{2-4}$-alkynyloxy, aryloxy, haloaryloxy, $C_{1-4}$-alkylaryloxy, aryl, haloaryl, $C_{1-4}$-alkylaryl or halo and X is oxygen, and $R_1$-aryl is phenyl, 1-naphthyl or 2-naphthyl, and $R_4$-aryl is phenyl.

2. A compound of claim 1 wherein $R_1$ is chlorophenyl, bromophenyl, fluorophenyl, methylphenyl, methoxyphenyl, ethoxyphenyl, difluoromethoxyphenyl or dimethoxyphenyl,
$R_2$ is methyl,
$R_3$ is hydrogen,
$R_4$ is phenoxyphenyl or fluorophenoxyphenyl.

3. 2-(4-Chlorophenyl)-2-difluoromethyl-1-(4-fluoro-3-phenoxybenzyloxy)propane, a compound of claim 1.

4. 2-(4-Chlorophenyl)-2-difluoromethyl-1-(3-phenoxybenzyloxy)propane, a compound of claim 1.

5. 2-Difluoromethyl-2-(4-methylphenyl)-1-(3-phenoxybenzyloxy)propane, a compound of claim 1.

6. 2-Difluoromethyl-1-(4-fluoro-3-phenoxybenzyloxy)-2-(4-methoxyphenyl)propane, a compound of claim 1.

7. 2-Difluoromethyl-2-(4-methoxyphenyl)-1-(3-phenoxybenzyloxy)propane, a compound of claim 1.

8. 2-Difluoromethyl-2-(4-fluorophenyl)-1-(fluoro-3-phenoxybenzyloxy)propane, a compound of claim 1.

9. 2-Difluoromethyl-2-(4-fluorophenyl)-1-(3-phenoxy-benzyloxy)propane, a compound of claim 1.

10. 2-Difluoromethyl-2-(4-ethoxyphenyl)-1-(3-phenoxybenzyloxy)propane, a compound of claim 1.

11. 2-Difluoromethyl-2-(4-ethoxyphenyl)-1-(4-fluoro-3-phenoxybenzyloxy)propane, a compound of claim 1.

12. 2-Difluoromethyl-1-(3-phenoxybenzyloxy)-2-(4-n-propoxyphenyl)propane, a compound of claim 1.

13. 2-Difluoromethyl-1-(4-fluoro-3-phenoxybenzyloxy)-2-(4-n-propoxyphenyl)propane, a compound of claim 1.

14. 2-Difluoro-2-(4-isopropoxyphenyl)-1(3-phenoxybenzyloxy)propane, a compound of claim 1.

15. 2-Difluoromethyl-1-(4-fluoro-3-phenoxybenzyloxy)-2-(4-isopropoxyphenyl)propane, a compound of claim 1.

16. 2-(4-n-Butoxyphenyl)-2-difluoromethyl-1-(3-phenoxybenzyloxy)propane, a compound of claim 1.

17. 2-(4-n-Butoxyphenyl)-2-difluoromethyl-1-(4-fluoro-3-phenoxybenzyloxy)propane, a compound of claim 1.

18. 2-(4-Allyloxyphenyl)-2-difluoromethyl-1-(3-phenoxybenzyloxy)propane, a compound of claim 1.

19. 2-(4-Allyloxyphenyl)-2-difluoromethyl-1-(4-fluoro-3-phenoxybenzyloxy)propane, a compound of claim 1.

20. 2-Difluoromethyl-2-[4-(2-fluoroethoxy)phenyl]-1-(3-phenoxybenzyloxy)propane, a compound of claim 1.

21. 2-Difluoromethyl-1-(4-fluoro-3-phenoxybenzyloxy)-2-(4-propargyloxyphenyl)propane, a compound of claim 1.

22. 2-(4-Difluoromethoxyphenyl)-2-difluoromethyl-1-(3-phenoxybenzyloxy)propane, a compound of claim 1.

23. 2-(4-Difluoromethoxyphenyl)-2-difluoromethyl-1-(4-fluoro-3-phenoxybenzyloxy)propane, a compound of claim 1.

24. 2-(4-Bromophenyl)-2-difluoromethyl-1-(3-phenoxybenzyloxy)propane, a compound of claim 1.

25. 2-(4-Bromophenyl)-2-difluoromethyl-1-(4-fluoro-3-phenoxybenzyloxy)propane, a compound of claim 1.

26. 2-(4-tert.-Butylphenyl)-2-difluoromethyl-1-(3-phenoxybenzyloxy)propane, a compound of claim 1.

27. 2-(4-tert.-Butylphenyl)-2-difluoromethyl-1-(4-phenoxybenzyloxy)propane, a compound of claim 1.

28. 2-Difluoromethyl-2-(2-naphthyl)-1-(3-phenoxybenzyloxy)propane, a compound of claim 1.

29. 2-Difluoromethyl-2-(2-naphthyl)-1-(4-fluoro-3-phenoxybenzyloxy)propane, a compound of claim 1.

30. 2-Difluoromethyl-2-(3,4-dimethoxyphenyl)-1-(3-phenoxybenzyloxy)propane, a compound of claim 1.

31. 2-Difluoromethyl-2-(3,4-dimethoxyphenyl)-1-(4-phenoxybenzyloxy)propane, a compound of claim 1.

32. 2-Difluoromethyl-1-(4-fluoro-3-phenoxybenzyloxy)-2-[4-(2-fluoroethoxy)-phenyl]propane, a compound of claim 1.

33. 2-Difluoromethyl-1-[3-(2-fluoroethoxy)benzyloxy]-2-(4-ethoxyphenyl)propane, a compound of claim 1.

34. 2-Difluoromethyl-1-[4-(2-fluoroethoxy)benzyloxy]-2-(4-ethoxyphenyl)propane, a compound of claim 1.

35. 2-Difluoromethyl-1-(3-phenoxybenzyloxy)-2-[4-(2,2,2-trifluoroethoxy)phenyl]propane, a compound of claim 1.

36. 2-Difluoromethyl-1-(4-fluoro-3-phenoxybenzyloxy)-2-[4-(2,2,2-trifluoroethoxy)phenyl]propane, a compound of claim 1.

37. 2-Difluoromethyl-2-(4-ethoxyphenyl)-1-(2-methyl-3-phenylbenzyloxy)propane, a compound of claim 1.

38. A compound of claim 1 wherein aryl in $R^1$ is phenyl, 1-naphthyl or 2-naphthyl.

39. A compound of claim 1 wherein $R_4$ is substituted phenyl.

40. A pesticidal composition comprising an amount of a compound of claim 1 and a pesticidally compatible adjuvant.

41. A composition of claim 40 wherein the amount of said compound is 10–90 percent by weight.

42. A composition of claim 40 wherein the concentration of said compound is 0.0005 to 5% in grams per 100 ml of composition.

43. A method of achieving a pesticidal effect in a location comprising treating the location with a compound of claim 1.

44. A method of claim 43 for achieving an insecticidal effect.

45. A method of claim 44 wherein the location is a crop site.

46. A compound of claim 1 wherein aryl is $R_1$ is phenyl.

* * * * *